US00PP18494P3

(12) United States Plant Patent
Stemkens

(10) Patent No.: US PP18,494 P3
(45) Date of Patent: Feb. 19, 2008

(54) ***VERBENA* PLANT NAMED 'CARSCA'**

(50) Latin Name: ***Verbena* hybrid**
Varietal Denomination: Carsca

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/367,960

(22) Filed: Mar. 3, 2006

(65) Prior Publication Data

US 2007/0209095 P1 Sep. 6, 2007

(51) Int. Cl.
*A01H 5/00* (2006.01)

(52) U.S. Cl. ..... Plt./308
(58) Field of Classification Search ..... Plt./308
See application file for complete search history.

(56) References Cited

PUBLICATIONS

UPOV–ROM GTITM, Plant Variety Database, 2006/04, GTI Jouve Retrieval Software, Citation for *Verbena* 'Carsca' one page.*

Syngenta Global retrieved from the Internet. Retrieved on Mar. 16, 2007 at <http://syngenta.com/en/site/printer_friendly.aspx> 3 pages.*

* cited by examiner

*Primary Examiner*—Kent Bell
*Assistant Examiner*—June Hwu
(74) *Attorney, Agent, or Firm*—Bruce Vrana

(57) ABSTRACT

A new and distinct variety of *Verbena* plant, substantially as herein illustrated and described, characterized particularly as to novelty by its scarlet flowers, early flowering and a habit that is very compact and later spreading.

1 Drawing Sheet

Latin name of the genus and species of the plant claimed: *Verbena* hybrid.
Varietal denomination: 'Carsca'.

BACKGROUND OF THE NEW PLANT

The present invention comprises a new distinct cultivar of *Verbena,* botanically known as *Verbena×hybrida.*

The new cultivar is propagated from cuttings resulting from the cross of 'B0977-1' and 'C1218-1'. 'B0977-1' is a burgundy flowering *Verbena* having a semi-erect habit. 'B0977-1' is not commercially available and is not known by any synonyms. 'C1218-1' is a scarlet flowering *Verbena.* 'C1218-1' is not commercially available and is not known by any synonyms. Neither 'B0977-1' nor 'C1218-1' have been patented.

As a result of this cross the present cultivar was created in 2001 in Enkhuizen, Netherlands and has been repeatedly asexually reproduced by cuttings in Enkhuizen, Netherlands and Sarrians, France over a three year period. The new variety is stable and reproduces true to type in successive generations of asexual reproduction.

This new *Verbena* plant is an annual in most climatical zones in the US, only in zones 9 and 10 is it a perennial plant.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Verbena.* The data which defines these characteristics were collected from asexual reproductions carried out in Enkhuizen, Netherlands. The plant history was taken on 14 weeks old plants blossomed under natural light in a greenhouse and grown in a 10.5 cm container.

Color readings were taken in the greenhouse under ambient light. Color references are primarily to The R.H.S. Colour Chart of The Royal Horticultural Society of London.

TABLE 1

Differences between the new cultivar 'Carsca,' its parents and a similar cultivar

| | 'Carsca' | 'B0977-1' | 'C1218-1' | 'Scarlena' |
|---|---|---|---|---|
| Plant habit | Compact | Compact | Vigorous | Vigorous |
| Flower color | Scarlet | Burgundy | Scarlet | Scarlet |
| Leaf color | Dark green | Medium green | Dark green | Medium green |

The commercial name of the most resembling variety is 'Tukana scarlet.' The patented name of this variety is 'Scarlena' and its U.S. Plant Pat. No. is 12,578.

The plant:
Classification: Botanical: *Verbena×hybrida.*
*Parentage.*—Female parent: A seedling named 'B0977-1' is one of our seedlings from our B-generation of plants. Pollen parent: A seedling named 'C1218-1' is one of our seedlings from our C-generation of plants.
*Growth habit.*—Compact, later spreading, decumbent.
*Plant height.*—12–15 cm.

*Spreading area of plant.*—34–48 cm.
*Branching character.*—Freely branching and lateral branching at every node.
*Number of branches per plant.*—20–28.
*Blooming period.*—From March until November.

The stem:
*Diameter.*—2–3 mm.
*Length.*—10–15 cm.
*Shape.*—Tetragonal.
*Anthocyanin pigmentation.*—Absent.
*Color of the stem.*—137C.
*Length of internode.*—28–54 mm.
*Pubescence.*—Slightly pubescent.
*Length lateral branches.*—15–19 cm.

The foliage:
*Phyllotaxis.*—Opposite.
*Shape of blade.*—Ovate.
*Texture.*—Upper side: Smooth. Lower side: Smooth.
*Venation.*—Pinnate.
*Leaf margin.*—Slightly incised.
*Leaf base.*—Obtuse.
*Leaf apex.*—Acute.
*Length.*—18–26 mm.
*Width.*—10–15 mm.
*Depth of incision.*—1–3 mm.
*Number of incisions.*—4–6 per leaf.
*Color.*—Upper side: 137A. Lower side: 137C.
*Pubescence.*—Some pubescence is present on the upper surface of the leaf.
*Length of petiole.*—2–4 mm.
*Petiole surface structure.*—Slightly pubescent.
*Petiole diameter.*—1 mm.
*Petiole coloration.*—143C.

The bud:
*Peduncle length.*—20–40 mm.
*Peduncle diameter.*—1–2 mm.
*Peduncle color.*—143C.
*Strength of the peduncle.*—Moderately strong.
*Budsize.*—Diameter: 2 mm. Length: 8–10 mm.
*Budshape.*—Elongated and ovate.
*Bud color.*—137C.
*Sepals.*—Color (Upper side): 143C. Color (Lower side): 143C. Form: Upright. Number: 5, fused. Length: 7–9 mm. Width: 2 mm. Shape: Elongated. Apex: Emarginate. Base: Fused. Margin: Entire.

The flower:
*Flower diameter.*—18–24 mm.
*Flower height.*—20–22 mm.
*Flower tube length.*—15–20 mm.
*Flower throat diameter.*—2–3 mm.
*Flower throat color.*—155C.
*Inflorescence.*—Corymb.
*Flower-form.*—Single, salverform, sessile on terminal corymbs.
*Petal color.*—Upper side: 45B. Lower side: 45D.
*Eye.*—A small (3 mm) whiteish Eye (N155C) is present on all petals at their base.
*Overlapping of petals.*—Separate.
*No. of petals.*—Gamopetalous, 5 lobed.
*Petal apex.*—Obcordate.
*Petal base.*—Fused.
*Petal margin.*—Entire.
*Petal surface texture.*—Smooth.
*Size of the petal.*—Length: 7–9 mm. Width: 6–8 mm.
*Inflorescence.*—Length: 20–35 mm. Diameter: 45–65 mm.
*Calyx length.*—12–14 mm.
*Calyx diameter.*—3–4 mm.
*Anthocyanin pigmentation of calyx limb.*—Absent.
*Color of the calyx.*—137B.
*No. of flowers per inflorescence.*—35–50.
*Fragrance.*—A very light rosy fragrance is present.
*Bloom time of one inflorescence.*—New florets continue to open in one corymb over a period of 14 days.
*Lastingness of one flower.*—2–4 days.

The reproductive organs:
*Androecium.*—Stamen quantity: 4. Anther shape: Ovoid. Anther length: 1 mm. Anther color: 145B. Pollen amount: No pollen.
*Gynoecium.*—Pistils quantity: 1. Pistil length: 2.0–2.4 cm, at end of growth from flower tube. Stigma shape: Bi-lobed. Stigma color: 145A. Style length: 1.9 cm. Style color: 144D. Ovary color: 144C.

Seeds: No seed set is observed.

Roots: Types of roots: Fibrous, color 155C. Roots start to grow on every part of the stem that contacts the soil, so not only at the nodes.

Physiological and ecological characteristics: Tolerates temperatures ranging from 4 to 35 degrees Celsius.

Disease/pest resistance: Plants of the new *Verbena* have not been noted to be resistant to specific pathogens and pests common to *Verbena*.

What is claimed is:

1. A new and distinct cultivar of *Verbena* plant named 'Carsca,' as substantially illustrated and described herein.

* * * * *

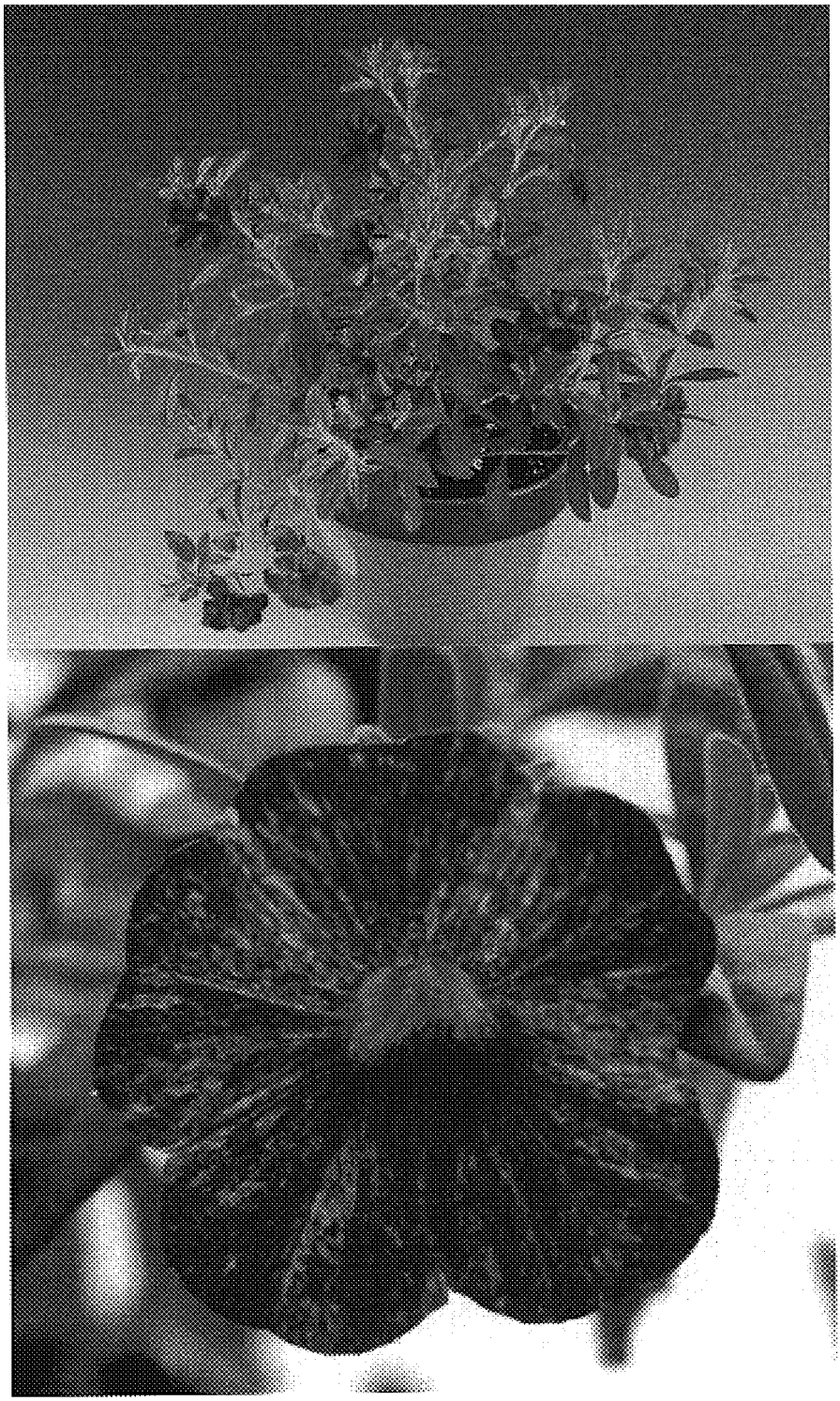

UNITED STATES PATENT AND TRADEMARK OFFICE

CERTIFICATE OF CORRECTION

PATENT NO. : PP 18,494 P3
APPLICATION NO. : 11/367960
DATED : February 19, 2008
INVENTOR(S) : Stemkens It is certified that error appears in the above-identified patent and that said Letters Patent is hereby corrected as shown below:

Delete Drawing sheet 1 and substitute therefor the color drawing sheet consisting of Figure 1 as shown on the attached page Signed and Sealed this Sixteenth Day of December, 2008

JON W. DUDAS
*Director of the United States Patent and Trademark Office*

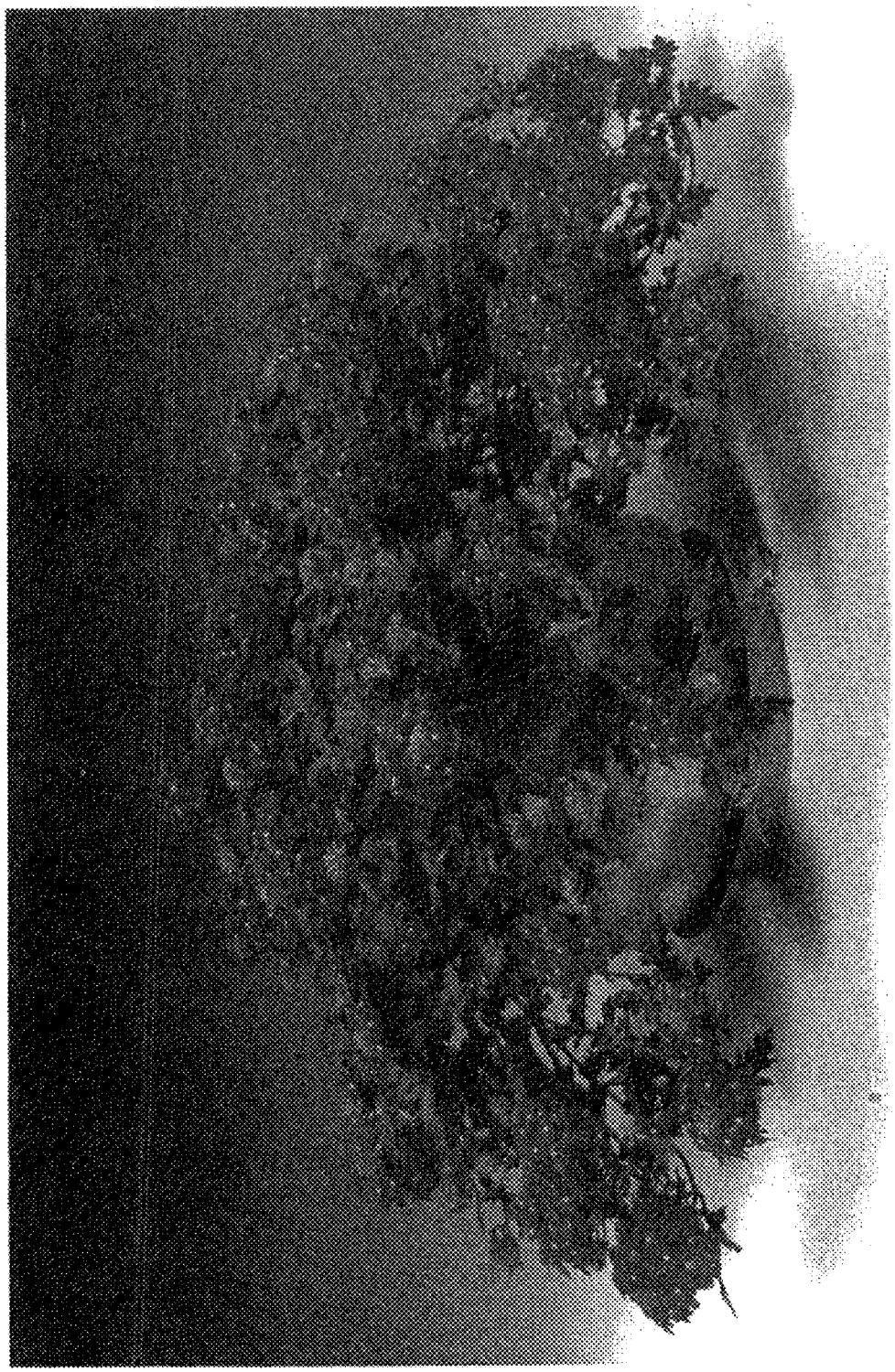

UNITED STATES PATENT AND TRADEMARK OFFICE

CERTIFICATE OF CORRECTION

PATENT NO. : PP 18,494 P3
APPLICATION NO. : 11/367960
DATED : February 19, 2008
INVENTOR(S) : Stemkens It is certified that error appears in the above-identified patent and that said Letters Patent is hereby corrected as shown below:

Delete Drawing sheet 1 and substitute therefor the color drawing sheet consisting of Figure 1 as shown on the attached page This certificate supersedes the Certificate of Correction issued December 16, 2008.

Signed and Sealed this

Thirteenth Day of January, 2009

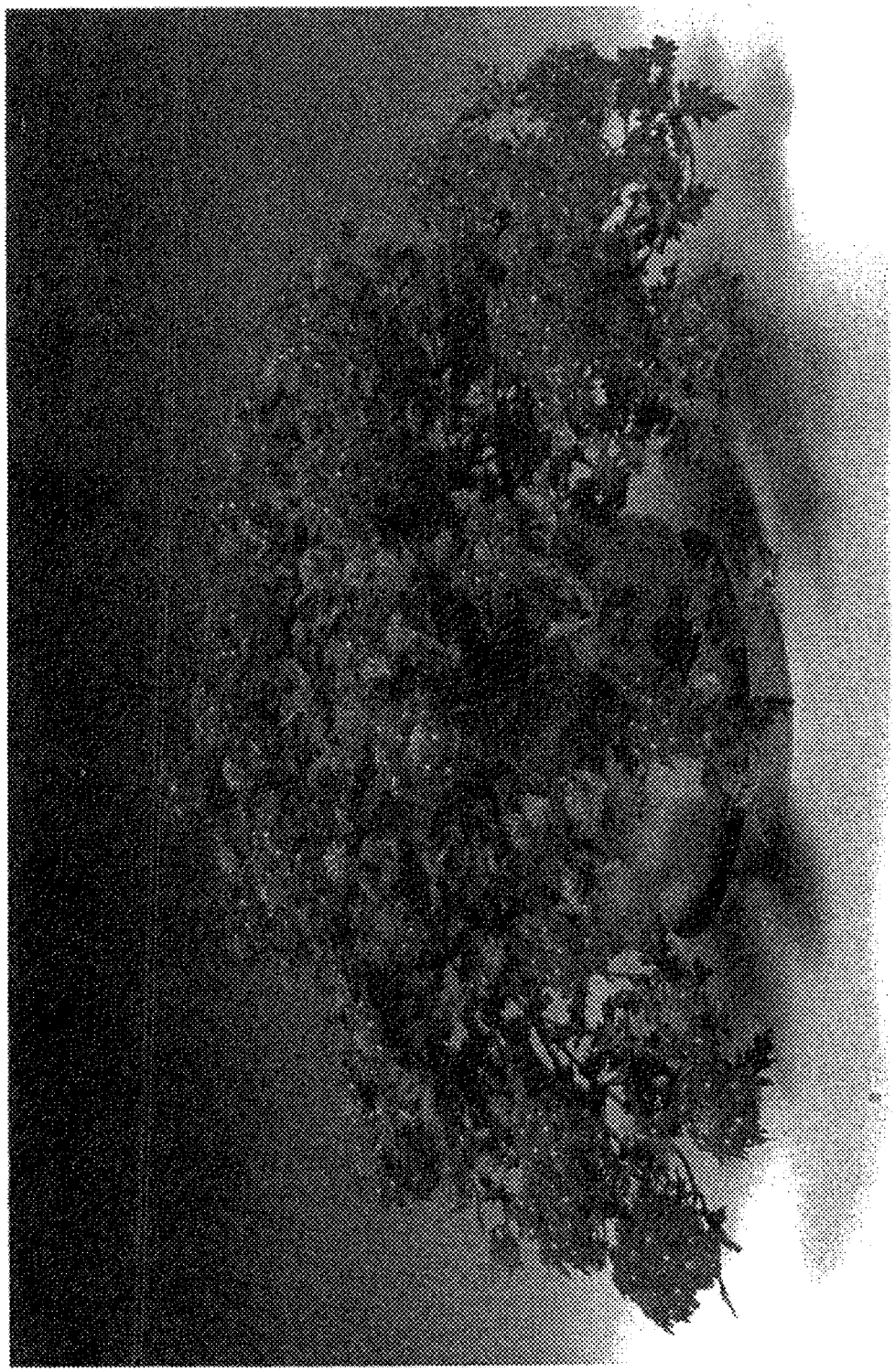

JON W. DUDAS
*Director of the United States Patent and Trademark Office*